US012799049B2

(12) United States Patent
Meier et al.

(10) Patent No.: US 12,799,049 B2
(45) Date of Patent: Nov. 17, 2026

(54) METHOD FOR ISOMERIZING OLEFINS

(71) Applicant: Evonik Oxeno GmbH & Co. KG, Marl (DE)

(72) Inventors: Ralf Meier, Sendenhorst (DE); Horst-Werner Zanthoff, Muelheim a.d. Ruhr (DE); Jan Benedikt Metternich, Recklinghausen (DE); Vinzenz Fleischer, Marl (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 119 days.

(21) Appl. No.: 19/102,510

(22) PCT Filed: Jun. 30, 2023

(86) PCT No.: PCT/EP2023/068063
§ 371 (c)(1),
(2) Date: Feb. 10, 2025

(87) PCT Pub. No.: WO2024/037771
PCT Pub. Date: Feb. 22, 2024

(65) Prior Publication Data

US 2026/0078072 A1 Mar. 19, 2026

(30) Foreign Application Priority Data

Aug. 16, 2022 (EP) .................................... 22190500

(51) Int. Cl.
*C07C 5/25* (2006.01)
*B01J 35/61* (2024.01)
*B01J 37/00* (2006.01)
*C07C 7/04* (2006.01)

(52) U.S. Cl.
CPC ........... *C07C 5/2512* (2013.01); *B01J 35/613* (2024.01); *B01J 35/615* (2024.01); *B01J 37/0009* (2013.01); *C07C 7/04* (2013.01); *C07C 2521/04* (2013.01); *C07C 2521/08* (2013.01)

(58) Field of Classification Search
CPC .... B01J 35/613; B01J 35/615; B01J 37/0009; C07C 5/2512; C07C 7/04; C07C 11/08; C07C 2521/04; C07C 2521/08
See application file for complete search history.

(56) References Cited

U.S. PATENT DOCUMENTS

| | | | | |
|---|---|---|---|---|
| 4,777,322 | A | 10/1988 | Hoelderich et al. | |
| 5,177,281 | A | 1/1993 | Haag et al. | |
| 11,174,207 | B2 | 11/2021 | Geilen et al. | |
| 2005/0070747 | A1 | 3/2005 | Brown et al. | |
| 2018/0057423 | A1 | 3/2018 | Kimura et al. | |
| 2020/0290940 | A1* | 9/2020 | Kramer | C07C 5/2518 |

FOREIGN PATENT DOCUMENTS

| | | | |
|---|---|---|---|
| EP | 0 170 182 | 2/1986 | |
| EP | 3 822 244 | 5/2021 | |
| EP | 3822244 A1 * | 5/2021 | C07C 5/2512 |
| WO | 2021/094162 | 5/2021 | |

OTHER PUBLICATIONS

International Search Report received for PCT Application No. PCT/EP2023/068063, mailed on Sep. 19, 2023, 6 pages with English translation.
Written Opinion received for PCT Application No. PCT/EP2023/068063, mailed on Sep. 19, 2023, 9 pages with English translation.

* cited by examiner

*Primary Examiner* — Vishal V Vasisth
(74) *Attorney, Agent, or Firm* — Grüneberg Global IP, PLLC

(57) ABSTRACT

A process isomerizes, in the presence of a heterogeneous catalyst which has silicon-aluminum mixed oxide composition, C4 to C9 olefins having a terminal double bond to the corresponding olefins having an internal double bond.

20 Claims, No Drawings

METHOD FOR ISOMERIZING OLEFINS

CROSS-REFERENCE TO RELATED APPLICATIONS

This application is a National Stage entry under § 371 of International Application No. PCT/EP2023/068063, filed on Jun. 30, 2023, and which claims the benefit of priority to European Application No. 22190500.3, filed on Aug. 16, 2022.

BACKGROUND OF THE INVENTION

Field of the Invention

The present invention relates to a process for the isomerization of C4 to C9 olefins having a terminal double bond to the corresponding olefins having an internal double bond, wherein a heterogeneous catalyst which comprises a silicon-aluminium mixed oxide composition is used.

Description of Related Art

In isomerizations (in the case of processes within a molecule the term "rearrangements" is also used), the starting molecule is converted into a molecule in which the molecular formula is unchanged, but the order or arrangement of the atoms or the arrangement of the bonds is altered Isomers often have comparable bond energies, with the result that interconversion can take place relatively freely. A distinction is made depending on the type of conversion, for example bond isomerization, in which double bonds are rearranged for example between C—C bonds (numerous bond isomerizations involving heteroatoms, such as O, N, P and S, are however also known to those skilled in the art); skeletal isomerization, in which linear compounds are rearranged into branched ones; hydroisomerization, in which an alkane is converted into an isomeric alkane in the presence of hydrogen via an alkene intermediate; or cis/trans isomerization, in which the substituents of a double bond are rearranged. Isomerizations are often accelerated by acidic/basic catalysts. The properties of the catalysts, such as the strength of the acid/base centres, essentially determine which of the isomerizations in a molecule take place. The isomerization that is desired here is a bond isomerization.

The corresponding olefins having a terminal or internal double bond may be provided by way of various processes, for example cracking processes. Another possibility is the catalytic isomerization of olefins having a terminal double bond to the corresponding olefins having an internal double bond. The degree of conversion is in each case limited by the thermodynamic equilibrium. Catalytic isomerization to olefins having a terminal double bond is known for example from EP 3 822 244 A1.

The general problem of isomerization reactions is that the olefins to be isomerized are, on account of their double bond, reactive molecules and therefore side reactions can occur. An example is oligomerization, which can take place on an acidic catalyst system and occurs as a side reaction to the isomerization when using acidic catalysts. In order to prevent oligomerization of the olefins during the isomerization to olefins having a terminal double bond, a basic catalyst system or catalysts doped with alkali metals or alkaline earth metals are used by preference.

The known catalyst systems have hitherto been disadvantageous in that they have exclusively been described for the isomerization of olefins having an internal double bond to olefins having a terminal double bond.

SUMMARY OF THE INVENTION

The object of the present invention was therefore to provide a process which gives preference to the isomerization of olefins having a terminal double bond to olefins having an internal double bond, particularly the isomerization of 1-butene to 2-butene. From an economic viewpoint, it should be possible for the isomerization to be performed at low temperatures, the shortest possible dwell times, high selectivity and a high conversion. The catalyst used here should also have long-term stability and as far as possible not promote side reactions such as oligomerization.

DETAILED DESCRIPTION OF THE INVENTION

It was surprisingly found that, in a departure therefrom, it is also possible to use (weakly) acidic, $SiO_2$-based catalysts having a certain aluminium oxide content, that is to say for example catalysts based on the silicon-aluminium mixed oxide compositions mentioned herein, which provide high activity for the isomerization with a good product selectivity. In addition, oligomerization as a side reaction is virtually or completely absent.

The process according to the invention is consequently a process for the isomerization of C4 to C9 reactant olefins having a terminal double bond to product olefins having an internal double bond, wherein a hydrocarbon mixture comprising at least the reactant olefins to be isomerized and product olefins is brought into contact with a heterogeneous catalyst, wherein the heterogeneous catalyst is an X-ray amorphous silicon-aluminium mixed oxide composition having the following composition:

a) 96% to 99.99% by weight of silicon oxide (calculated as $SiO_2$); and
b) 0.01% to 4% by weight of aluminium oxide (calculated as $Al_2O_3$).

The X-ray amorphous silicon-aluminium mixed oxide composition used as catalyst may be produced by means of flame hydrolysis according to the process disclosed inter alia in DE 198 47 161 A1 or EP 0 850 876 A1. In this so-called "co-fumed process", volatile silicon and aluminium compounds, for example silicon tetrachloride and aluminium trichloride, are sprayed into an oxyhydrogen flame composed of hydrogen and oxygen or air, causing the silicon and aluminium compounds to be hydrolysed by means of the water formed in the oxyhydrogen flame and resulting in the formation of the mixed oxide composition.

An alternative process likewise disclosed in the documents mentioned is the so-called doping process. In this process, an oxide, in this case for example silicon oxide, is produced in the oxyhydrogen flame from its volatile compound (for example silicon tetrachloride) by flame hydrolysis in tandem with the introduction into the oxyhydrogen flame of an aerosol containing a salt of the element to be doped, in this case for example aluminium, resulting in the formation of the corresponding mixed oxide. The silicon-aluminium mixed oxide composition thus produced by flame hydrolysis is predominantly to entirely amorphous.

The X-ray amorphous silicon-aluminium mixed oxide compositions produced by means of the production processes mentioned by way of example are notable for their high chemical purity and have the following composition:

a) 96% to 99.99% by weight of silicon oxide, preferably 98.5% to 99.95% by weight of silicon oxide (calculated as $SiO_2$); and
b) 0.01% to 4% by weight of aluminium oxide, preferably 0.05% to 1.5% by weight of aluminium oxide (calculated as $Al_2O_3$).

In a preferred embodiment of the present invention, the silicon-aluminium mixed oxide composition additionally comprises alkali metal oxides and/or alkaline earth metal oxides, particularly preferably in an amount of up to 1% by weight based on the total composition. In order to introduce the alkali metal oxides or alkaline earth metal oxides, the mixed oxide composition produced by flame hydrolysis may be treated with an aqueous solution of the alkali metal hydroxide or alkaline earth metal hydroxide. This can be done for example by wetting or impregnating the mixed oxide composition produced by flame hydrolysis with a solution of the alkali metal salt and/or alkaline earth metal salt. The treated mixed oxide composition is then washed with water, dried at 100° C. to 150° C. and calcined at 300° C. to 600° C., preferably at 450° C. to 550° C. Silicon oxides and aluminium oxides may per se also already contain traces of alkali metals or alkaline earth metals, which are not taken into account here.

The silicon-aluminium mixed oxide compositions of the present invention may additionally be treated with an acidic, aqueous solution containing a phosphorus source. The phosphorus source used may be phosphoric acid, phosphonic acid, phosphinic acid, polyphosphoric acid or dihydrogen phosphate, preferably phosphoric acid. For this purpose, the mixed oxide composition is first suspended in water and the resulting suspension is then admixed with the phosphorus source, preferably such that the pH is in the range from 0 to 6, further preferably in the range from 1 to 2.5, particularly preferably in the range from 2 to 2.5. The treated mixed oxide composition is then washed with water, dried at 100° C. to 150° C. and calcined at 300° C. to 600° C., preferably at 450° C. to 550° C.

In a preferred embodiment, the silicon-aluminium mixed oxide composition according to the invention is predominantly (i.e. >70%) or entirely present in the form of aggregated primary particles. The silicon-aluminium mixed oxide composition here inter alia has the feature that the weight ratio $(Al_2O_3/SiO_2)_{surface}$ of the primary particles in the near-surface region is smaller than the weight ratio $(Al_2O_3/SiO_2)_{total}$ in the totality of the primary particles. The term "near-surface region" refers here to the region from the surface down to a depth of 5 nm. The difference in the weight ratios means that the aluminium oxide concentration at the surface is lower than in the overall composition. The totality of the primary particles includes the silicon dioxide and aluminium oxide fraction in the near-surface region.

Preference is therefore given to a silicon-aluminium mixed oxide composition that is predominantly or entirely present in the form of aggregated primary particles in which I) the weight ratio $(Al_2O_3/SiO_2)_{total}$ in the totality of the primary particles is 0.002 to 0.05, preferably 0.003 to 0.015, more preferably 0.005 to 0.01; and
II) the weight ratio $(Al_2O_3/SiO_2)_{surface}$ of the primary particles in the near-surface region is lower than in the totality of the primary particles.

The weight ratio $(Al_2O_3/SiO_2)_{surface}$ at the surface may be determined for example by X-ray-induced photoelectron spectroscopy (XPS analysis) of the powder. Additional information about the surface composition may be determined by energy-dispersive X-ray analysis (TEM-EDX analysis) of individual primary particles. The weight ratio $(Al_2O_3/SiO_2)_{total}$ in the totality of the primary particles may be determined by chemical or physicochemical methods, e.g. X-ray fluorescence analysis, on the powder The silicon-aluminium mixed oxide composition used as catalyst in the present invention is X-ray amorphous. "X-ray amorphous" in the context of the present invention means that an X-ray amorphous substance does not exhibit a crystalline structure in the X-ray diffractogram down to the detection limit of 5 nm.

The described silicon-aluminium mixed oxide composition according to the invention, in particular having the composition stated above and in particular having the stated differences in the weight ratios $(Al_2O_3/SiO_2)$, preferably has a BET surface area of 50 to 250 $m^2/g$, preferably 100 to 200 $m^2/g$ (determined in accordance with DIN ISO 9277 (version: 2014-01).

In addition, it may be advantageous when the silicon-aluminium mixed oxide composition has a dibutyl phthalate number, in g of dibutyl phthalate (DBP)/100 g of mixed composition, of 300 to 350. The DBP number is a measure of the structure of aggregates. Low numbers correspond to a low structure, and high numbers correspond to a high structure. The described range of 300 to 350 for the mixed oxide composition according to the invention corresponds to a high structure. In the case of DBP absorption, the force absorption, i.e. the torque (in Nm), of the rotating blades of the DBP measuring device is measured on addition of defined amounts of DBP. For the silicon-aluminium mixed oxide composition, this preferably gives a sharply defined maximum with a subsequent decrease on addition of a specific amount of DBP. The dibutyl phthalate absorption may be measured for example with a Rheocord 90 device from Haake, Karlsruhe. For this purpose, 12 g of the silicon-aluminium mixed oxide powder is introduced into a kneading chamber which is closed with a lid, and dibutyl phthalate is metered in through a hole in the lid at a defined metering rate of 0.0667 ml/s. The kneader is operated at a motor speed of 125 revolutions per minute. Once the maximum torque has been reached, the kneader and the DBP metering are automatically switched off. The amount of DBP consumed and the amount of particles weighed in are used to calculate the DBP absorption according to: DBP number (g/100 g)=(DBP consumption in g/weight of powder in g)×100.

For industrially operated isomerization using a catalyst that comprises the silicon-aluminium mixed oxide composition, a reaction regime taking place in one or more fixed-bed reactors is preferred. For liquid-phase reactions, it is also possible to use slurry reactors or trickle-bed reactors. Other reactor types, such as fluidized-bed reactors or moving-bed reactors, may also be used. For this purpose, it is necessary for the above-described mixed oxide composition produced by flame hydrolysis or pyrogenically to be shaped with addition of a binder by means of a shaping process known to those skilled in the art, particularly into the shape of granules, pellets or shaped bodies, such as tablets, cylinders, spheres, strand extrudates or rings. Suitable binders are known to those skilled in the art; for example alumina, ceramic clays, colloids or else amorphous zeolites are used.

For shaping, 1% to 20% by weight of the silicon-aluminium mixed oxide composition is first mixed with one of the abovementioned binders and additionally with temporary auxiliaries, such as water, aqueous solutions, water substitutes, such as glycols and polyglycols, and optionally further auxiliaries, such as fixatives, for example cellulose ethers, and/or plasticizers, for example polysaccharides, and/or pressing agents, for example nonionic wax dispersions. This procedure may be carried out in devices known to those skilled in the art, for example in a kneader or an intensive mixer. This is followed by the actual shaping by way of a shaping process, such as pelleting, extrusion or dry pressing. Before installation in the fixed-bed reactor(s), the shapes or shaped bodies are calcined in a temperature range from 200° C. to 700° C., resulting in the removal of at least the temporary auxiliaries.

The silicon-aluminium mixed oxide composition may be applied to a support that is inert in respect of the isomerization, for example a support made of metal, plastic or ceramic. If the silicon-aluminium mixed oxide composition is applied to an inert support, the mass and composition of the inert support is not taken into account in the determination of the composition of the silicon-aluminium mixed oxide composition.

The process according to the invention is carried out with the above-described silicon-aluminium mixed oxide composition as catalyst in order to isomerize C4 to C9 reactant olefins having a terminal double bond, preferably C4 to C8 reactant olefins having a terminal double bond, further preferably C4 to C6 reactant olefins having a terminal double bond, particularly preferably C4 reactant olefins having a terminal double bond, to product olefins having an internal double bond.

The olefins are not necessarily used in pure form, but in industrially available hydrocarbon mixtures. The isomerization consequently results in an increase in the content of the product olefin in the hydrocarbon mixture with a simultaneous decrease in the content of reactant olefin.

C5 olefins are present in light petroleum fractions from refineries or crackers. Industrial mixtures comprising linear C4 olefins are light petroleum fractions from refineries, C4 fractions from FC crackers or steam crackers, mixtures from Fischer-Tropsch syntheses, mixtures from the dehydrogenation of butanes and mixtures formed by metathesis or from other industrial processes.

Preferably, mixtures of linear butenes suitable for the process according to the invention may be obtained from the C4 fraction of a steam cracker. 1,3-Butadiene may be removed here in a preliminary step. This is accomplished either by extraction (or extractive distillation) of the butadiene or by selective hydrogenation thereof. In both cases, a practically butadiene-free C4 cut is obtained, referred to as raffinate I. The now butadiene-free C4 cut, referred to as raffinate I, comprises isobutene, the linear butenes and any butanes.

According to the invention, the reactant olefins are olefins having a terminal double bond that are converted by the isomerization at least partially into product olefins, that is to say olefins having an internal double bond. In a preferred embodiment, the reactant olefin is 1-butene or hydrocarbon mixtures comprising 1-butene which is converted by the isomerization according to the invention into cis- and/or trans-2-butene. This enables the enrichment of 2-butenes in order to facilitate the distillative removal of isobutene. This has the advantage that energy can be saved and a significantly greater throughput can be achieved using the same apparatuses. 2-Butene may subsequently be oligomerized to C8 olefins, it being possible in turn to make plasticizer alcohols therefrom.

The conversion of the reactant olefin into the product olefin is limited at the lower end in particular by the temperature-dependent position of the chemical equilibrium of the isomerization reaction. The advantage of using a catalyst according to the invention is that the conversion corresponds to the conversion at thermodynamic equilibrium in a broader temperature range or is only marginally lower than this. This also applies to the isomerization of 1-butene to 2-butene, which is limited by the thermodynamic equilibrium of the n-butene isomers. The thermodynamic equilibrium of a mixture comprising 2-butenes and 1-butene is shifted by high temperatures in the direction of 1-butene. The thermodynamic equilibrium for 1-butene at a temperature of 25° C. is approximately 3% and at a temperature of 500° C. is approximately 29%.

For the isomerization process according to the invention, it is preferable to use at least one fixed-bed reactor. Other reactor types, such as fluidized-bed reactors, moving-bed reactors, slurry reactors or trickle-bed reactors, may also be used.

The process according to the invention may be carried out at atmospheric pressure. Higher reaction pressures may however also be employed. Operation under pressure in the process according to the invention is for example useful when the product olefin from the isomerization process according to the invention is fed to an additional separation stage that is likewise operated under pressure.

The isomerization according to the invention of olefins having a terminal double bond to olefins having an internal double bond, in particular of 1-butene to 2-butene, is performed preferably at a temperature between 20° C. and 250° C., further preferably between 35° C. and 200° C. and particularly preferably between 45° C. and 160° C. The gas hourly space velocities (GHSV) may be from 5 to 500 $h^{-1}$, preferably from 10 to 250 $h^{-1}$. The selectivity of the isomerization according to the invention in respect of the product olefin is preferably greater than 85%, further preferably greater than 90% and particularly preferably greater than or equal to 95%.

If the activity and selectivity of the catalyst according to the invention declines as a result of carbon deposits on the catalyst, the catalyst is expediently regenerated. An advantageous method of catalyst regeneration is to burn off the carbon deposits on the deactivated catalyst in oxygen-containing gases, preferably in air. It may be expedient here to dilute the air with nitrogen. The catalyst regeneration is generally carried out at temperatures of 350° C. to 600° C., preferably of 400° C. to 450° C. This generally allows the initial activity and the initial selectivity of the catalyst according to the invention to be recovered in a simple manner.

The present invention further provides a process for the distillative removal of isobutene from C4 hydrocarbon streams comprising at least isobutenes, 1-butenes and 2-butenes, wherein the process comprises the following steps:

1) carrying out an isomerization with the C4 hydrocarbon stream, whereby the 1-butenes in the C4 hydrocarbon stream are at least partially converted into 2-butenes, wherein the C4 hydrocarbon stream is brought into contact with a heterogeneous catalyst, wherein the heterogeneous catalyst is a silicon-aluminium mixed oxide composition having the following composition:
   a) 96% to 99.99% by weight, preferably 98.5% to 99.95% by weight, of silicon oxide (calculated as $SiO_2$); and
   b) 0.01% to 4% by weight, preferably 0.05% to 1.5% by weight, of aluminium oxide (calculated as $Al_2O_3$); and
2) carrying out a distillative removal in order to remove isobutene from the C4 hydrocarbon stream.

The distillative removal of isobutene from the C4 hydrocarbon stream is known in principle to those skilled in the art. The distillation in step 2) is preferably carried out at a pressure from 1-10 bar, preferably from 2 to 8 bar. The temperature in the distillation in step 2) is preferably 20° C. to 80° C., particularly preferably 25° C. to 70° C. Furthermore, the distillation in step 2) may be carried out using known distillation columns. The column may comprise a plurality of trays and/or separation stages.

The present invention further provides a two-stage isomerization with a distillation in between. The first stage involves carrying out the isomerization described above, that is to say an isomerization of C4 to C9 reactant olefins, preferably C4 olefins, having a terminal double bond, preferably 1-butenes, to product olefins having an internal double bond, preferably 2-butenes, wherein a hydrocarbon mixture comprising at least the reactant olefins to be isomerized and product olefins is brought into contact with a heterogeneous catalyst, wherein the heterogeneous catalyst is a silicon-aluminium mixed oxide composition having the following composition:

a) 96% to 99.99% by weight, preferably 98.5% to 99.95% by weight, of silicon oxide (calculated as $SiO_2$); and b) 0.01% to 4% by weight, preferably 0 05% to 1.5% by weight, of aluminium oxide (calculated as $Al_2O_3$).

The isomerization is followed by a distillation, in which the removed reactant olefins having a terminal double bond, preferably the 1-butenes together with the isobutenes, are removed from the product olefins having an internal double bond, preferably the 2-butenes. Appropriate processes and the respective conditions are familiar to those skilled in the art.

The removed reactant olefins, preferably the mixture of 1-butenes and isobutenes that is obtained from the removal, are then subjected in a second step to a further isomerization. The catalyst used may be the silicon-aluminium mixed oxide composition that is also used in the first step and has the following composition:

a) 96% to 99.99% by weight, preferably 98.5% to 99.95% by weight, of silicon oxide (calculated as $SiO_2$); and b) 0.01% to 4% by weight, preferably 0.05% to 1.5% by weight, of aluminium oxide (calculated as $Al_2O_3$).

In the second step, it is possible for other reactions, for example dimerizations of the olefins obtained, to also occur in addition to the isomerization. In the case of C4 olefins, the isobutenes can in particular dimerize to form diisobutenes, which however can then also quite easily be separated off and marketed.

The present invention is described below with reference to an example. This serves for elucidation and does not constitute a restriction of the subject matter of the invention.

EXAMPLE 1

11.7 g of a catalyst according to the invention (AEROSIL® MOX170, approx. 1% by weight of aluminium oxide, BET surface area between 140 and 200 $m^2/g$) is introduced into a tubular reactor with a diameter of 1 cm after 1:1 dilution with glass beads. The reactor was charged with 1-butene (>99%). This 1-butene was conducted through the reactor with different volumetric flow rates. The isomerization was effected at temperatures of 80° C. to 140° C. and ambient pressure. In the reaction, the conversions of 1-butene and the formation of 2-butene were determined. The analysis was effected by gas chromatography. The peak areas were evaluated according to the external calibration method.

| Vol. flow rate of 1-butene [ml/h] | Temperature [°C] | Conversion of 1-butene [%] | Selectivity for the formation of 2-butene [%] |
|---|---|---|---|
| 250 | 80 | 90.2 | 98.1 |
| 250 | 140 | 89.5 | 94.9 |
| 420 | 80 | 88.9[a] | 98.2[a] |

[a]Over a test time of 500 hours.

The results show that the catalysts according to the invention are very well suited to the isomerization. It can further be seen that hardly any side reactions occur; rather, high selectivities for 2-butene can be achieved. This also applies to long-term tests with a test duration of more than 500 hours.

The invention claimed is:

1. A process for the isomerization of C4 to C9 reactant olefins having a terminal double bond to product olefins having an internal double bond, the process comprising:

bringing into contact a hydrocarbon mixture comprising at least the reactant olefins to be isomerized with a heterogeneous catalyst, wherein the heterogeneous catalyst is an X-ray amorphous silicon-aluminium mixed oxide composition having the following composition:

a) 96% to 99.99% by weight of silicon oxide (calculated as $SiO_2$); and b) 0.01% to 4% by weight of aluminium oxide (calculated as $Al_2O_3$).

2. The process according to claim 1, wherein the silicon-aluminum mixed oxide composition has the following composition:

a) 98.5% to 99.95% by weight of silicon oxide (calculated as $SiO_2$); and b) 0,05% to 1.5% by weight of aluminium oxide (calculated as $Al_2O_3$).

3. The process according to claim 1, wherein the silicon-aluminum mixed oxide composition has a BET surface area of 50 to 250 $m^2/g$.

4. The process according to claim 1, wherein the heterogeneous catalyst consists of shaped bodies produced from the silicon-aluminum mixed oxide composition in a shaping process with addition of binders and at least temporary auxiliaries.

5. The process according to claim 1, wherein the content of the product olefin in the hydrocarbon mixture is increased as a result of the isomerization.

6. The process according to claim 1, comprising:

carrying out the isomerization at a temperature between 20 °C and 250 °C.

7. The process according to claim 1, wherein a gas hourly space velocity during the isomerization is from 5 to 500 $h^{-1}$.

8. The process according to claim 1, wherein the reactant olefins are C4 to C8 reactant olefins having a terminal double bond.

9. The process according to claim 8, wherein the reactant olefins are 1-butene or hydrocarbon mixtures comprising 1-butene, and the product olefin having an internal double bond is cis- and/or trans-2-butene.

10. The process according to claim 1, wherein the silicon-aluminum mixed oxide composition is predominantly or entirely present in a form of aggregated primary particles.

11. The process according to claim 10, wherein the silicon-aluminum mixed oxide composition has a feature that a weight ratio $(Al_2O_3/SiO_2)_{surface}$ of the aggregated primary particles in a near-surface region is smaller than a weight ratio $(Al_2O_3/SiO_2)_{total}$ in a totality of the aggregated primary particles.

12. The process according to claim 10, wherein the silicon-aluminum mixed oxide composition is predominantly or entirely present in the form of aggregated primary particles in which I) the weight ratio of $(Al_2O_3/SiO_2)_{total}$ in the totality of the aggregated primary particles is 0.002 to 0.05; and II) the weight ratio $(Al_2O_3/SiO_2)_{surface}$ of the aggregated primary particles in a near-surface layer having a thickness of 5 nm is less than in the totality of the aggregated primary particles.

13. A process for the distillative removal of isobutene from C4 hydrocarbon streams comprising at least isobutene, 1-butene and 2-butene, the process comprising:

1) carrying out an isomerization according to claim 1, wherein the 1-butene in the C4 hydrocarbon stream is at least partially converted into 2-butene;

2) carrying out a distillative removal in order to remove isobutene and 1-butene from the C4 hydrocarbon stream.

14. The process according to claim 13, comprising:

carrying out the isomerization in two stages, wherein after the distillation in 2) the mixture of 1-butene and isobutene obtained from the distillative removal is subjected in a second step to a further isomerization.

15. The process according to claim 1, wherein the silicon-aluminum mixed oxide composition has a BET surface area of 100 to 220 $m^2/g$.

16. The process according to claim 1, comprising: carrying out the isomerization at a temperature between 45 °C and 160 °C.

17. The process according to claim 1, wherein a gas hourly space velocity during the isomerization is from 10 to 250 $h^{-1}$.

18. The process according to claim 1, wherein the reactant olefins are C4 to C6 reactant olefins having a terminal double bond.

19. The process according to claim 9, wherein the selectivity of the isomerization in respect of the product olefin is greater than 85%.

20. The process according to claim 9, wherein the selectivity of the isomerization in respect of the product olefin is greater than 95%.

* * * * *